United States Patent [19]

Lundy

[11] Patent Number: 4,512,977

[45] Date of Patent: Apr. 23, 1985

[54] THERAPEUTIC SELENIUM COMPOSITIONS AND THE USE THEREOF

[75] Inventor: Joseph R. Lundy, New York, N.Y., Now by change of name from Joseph R. Levitt

[73] Assignee: Lundy Research Laboratories, Inc., New York, N.Y.

[21] Appl. No.: 386,113

[22] Filed: Jun. 7, 1982

Related U.S. Application Data

[60] Division of Ser. No. 86,391, Oct. 18, 1979, Pat. No. 4,340,590, which is a continuation-in-part of Ser. No. 821,156, Aug. 2, 1977, abandoned.

[51] Int. Cl.³ .................... A61K 33/04; A61K 33/38
[52] U.S. Cl. .................................. 424/132; 424/162
[58] Field of Search ............................. 424/132, 162

[56] References Cited

U.S. PATENT DOCUMENTS 3,928,578 12/1975 Burns et al. .................... 424/164

OTHER PUBLICATIONS

Chemical Abstracts, vol. 85:8817a, (1976).
Roberts, Toxicology and Applied Pharmacology, 5, pp. 500–506, (1963).
Rogers' Inorganic Pharmaceutical Chemistry, by Soine et al., published by Henry Kimpton, London, 1957, pp. 587–588.
Cohen, L. B., Amer. J. Ophth. 38, 560–562, (1954).
Slinger et al., Arch. Dermat. and Syph. 64, pp. 41–48, (1951).

*Primary Examiner*—Stanley J. Friedman
*Attorney, Agent, or Firm*—Morgan, Finnegan, Pine, Foley & Lee

[57] ABSTRACT

There are provided therapeutic compositions comprising certain selenium-containing compounds which exhibit therapeutic benefits in mammal hosts including humans. The selenium compounds in accordance with this invention are preferably water soluble organic or inorganic compounds containing selenium such as alkali metal selenites and selenates. Among the therapeutic benefits exhibited by these compositions are the reduction in severity from and improvements in recovery from physically induced damage to body tissue which includes damage caused by surgical incisions, lacerations and burns.

21 Claims, 1 Drawing Figure

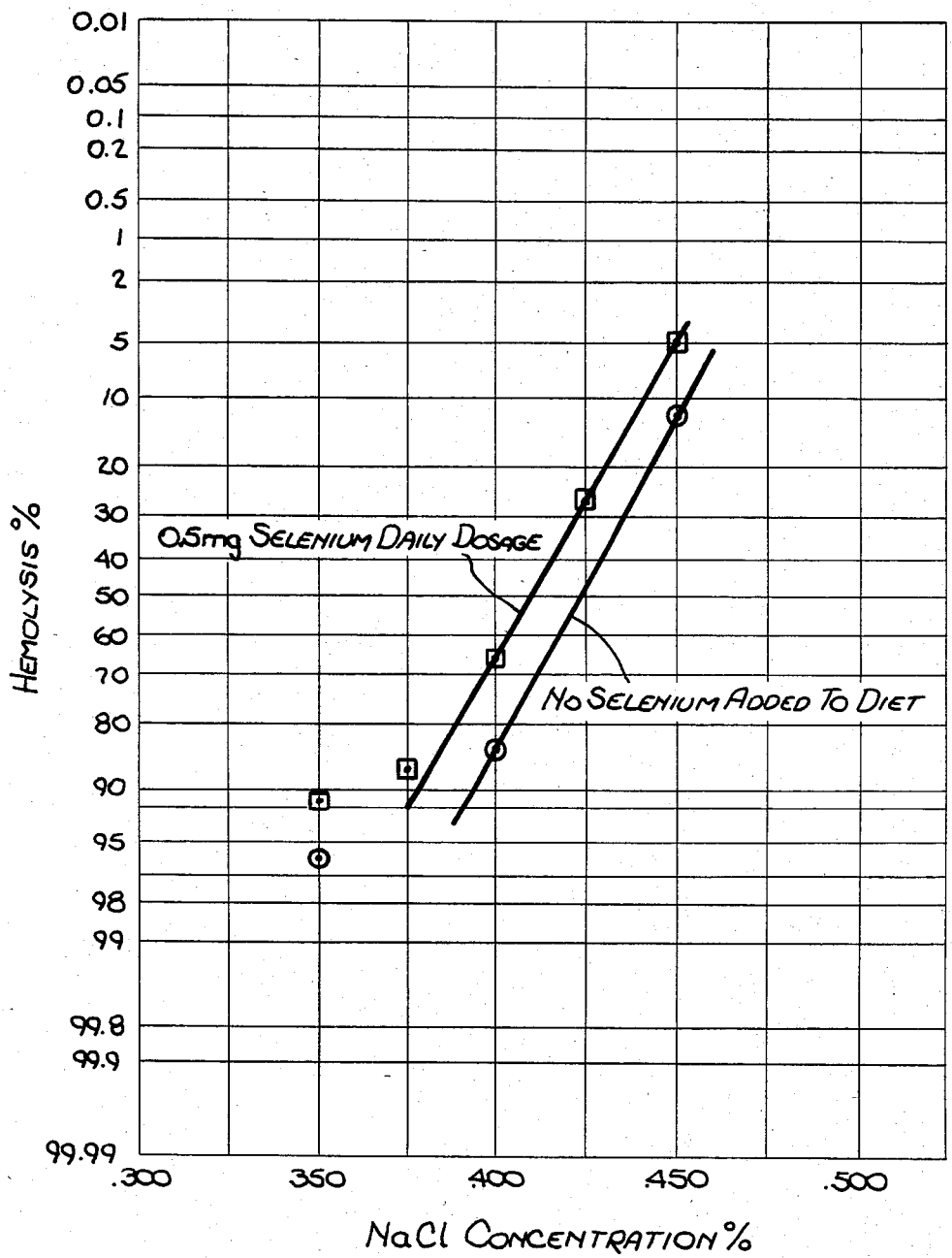

THERAPEUTIC SELENIUM COMPOSITIONS AND THE USE THEREOF

This is a division of application Ser. No. 86,391 filed Oct. 18, 1979, now U.S. Pat. No. 4,340,590, which in turn is a continuation-in-part of application Ser. No. 821,156 filed Aug. 2, 1977, now abandoned.

BACKGROUND OF THE INVENTION

This invention relates to therapeutic compositions containing certain selenium compounds. These therapeutic compositions have been found to exhibit surprising and unexpected properties in mammalian hosts. More particularly, the selenium compounds in accordance with the present invention are water soluble organic or inorganic compounds containing selenium in a form capable of being absorbed by the body tissue to be treated. Preferably, the compounds are salts containing selenium in the form of the selenite or selenate anions. In the practice of the present invention, the therapeutic compositions are formulated so that said selenium compound are present to certain specific amounts and concentrations so that they are non-toxic yet therapeutically active.

Selenium is one of numerous elements found in trace amounts in many foods. The selenium is present in many chemicals and often in very complex forms. Many technical studies have been carried out concerning its biological effects although the majority of the work has dealt with those adverse effects which occur by ingesting more than trace amounts of selenium-containing compounds.

Research studies to date have indicated that selenium does have beneficial physiological effects on mammals. For example, it is known that selenium, when ingested, reduces the rate of oxidative damage caused by chemicals, such as, for example, ozone in smog, by entering the membranes of the body's cells and protecting the contents of the cells from reacting with oxygen in a manner that damages the cells. It has also been reported that selenium may be beneficial in the treatment of heart disease by reducing or decreasing coronary vascular resistance in dogs. Additional studies have also shown some beneficial effects of selenium in cancer therapy. In combination with Vitamin E, selenium has been reported to have a beneficial effect in relief of arthritis and tendonitis.

On the other hand, there has been considerable reluctance to prescribe usages of selenium because of its apparent toxic effects when present in large dosages. While numerous medical and governmental reports have found selenium to have general toxic properties in adult mammals, there is no consensus as to specific toxicity levels nor toxicity effects.

It is known, however, that deleterious effects on the heart, lungs, liver and kidneys do occur, in addition to adverse effects on other body systems in mammals, both humans and animals, in cases where selenium is ingested. But the particular amounts ingested which cause such effects vary widely depending upon the form of the ingested selenium, and the presence of other materials in the diet of the host. For example, protein is reported to afford some protection against the toxic effects of selenium.

It is therefore surprising that in accordance with the present invention it has been discovered that pharmaceutically safe compositions have been formulated which have unexpected therapeutic and physiological properties and benefits which enable it to be easily formulated and administered to mammals, including humans. Also provided by this invention are methods of treating mammals, including humans, to reduce the severity from and to improve recovery from certain physically induced injuries to tissue, particularly soft body tissue, caused by physical effects or irritating stimuli such as surgical operations, lacerations, and burns including electrical, sun and thermal burns, etc.

SUMMARY OF THE INVENTION

In accordance with the present invention, there are provided therapeutic compositions for treating mammals, including humans, comprising a therapeutically effective but non-toxic amount of a water soluble organic or inorganic selenium compound combined with a pharmaceutically acceptable carrier or vehicle therefor. In general, such compositions comprise about 0.05 mg to about 2.0 mg and preferably 0.5 to 1.0 mg of elemental selenium by weight, based on the total weight of the composition, in the finished dosage form.

The selenium compound is preferably a water soluble organic or inorganic selenite or selenate such as alkali metal or silver selenites or selanates. The composition may be formulated for oral, injectable, topical or suppository administration. For example, tablets, capsules, solutions, creams and the like may be made where the selenium compound is dispersed substantially homogeneously throughout a suitable pharmaceutically acceptable carrier or vehicle in such finished dosage form.

DESCRIPTION OF THE PREFERRED EMBODIMENTS

Compositions in accordance with the present invention which contain certain selenium compounds in therapeutically effective but non-toxic dosages can be administered to mammals for the purpose of reducing the severity from and improving the recovery from physically induced damage to the host's tissue, particularly soft body tissue. By physically induced damage is meant various types of damage to the tissue of a mammal including, for example, surgical incisions, lacerations, burns, etc. Accompanying such damage are the likelihood of infection, edema, ecchymosis and other inflammatory responses. It has been found that where the therapeutic compositions of the present invention are administered prior to such physically induced damage to tissue, such as prior to surgery, an observable improvement in the patient's healing of the tissue and a reduced degree of infection, edema, ecchymosis and other inflammatory responses are noted.

It has also been found that the therapeutic composition of the present invention can be administered subsequent to the physically induced damage to tissue and improve the recovery of the tissue and affected areas. For example, the compositions of the present invention may be applied topically to the specifically affected areas of the skin to reduce scarring, etc.

It is also intended that physically induced damage in accordance with the present invention should include damage due to burns. It has been found that lesions and scars to the skin due to burning and other tissue damage is reduced and in some cases eliminated and that recovery is accelerated by use of the composition of the present invention.

The anti-inflammatory properties of the selenium compositions of this invention provide useful advantages when employed alone or with other materials utilized, for example, in pre-operative or post-operative surgical procedures. For example, various compounds such as steroids have been alleged to possess anti-inflammatory properties. Included among these are, for example, cortisone and hydrocortisone.

The selenium compositions of this invention used alone exhibit effective anti-inflammatory properites without the detrimental side efects of some known materials which exhibit anti-inflammatory properties. The selenium compounds of the present invention may be combined with materials having compatible properties to form compositions exhibiting the beneficial effects of the selenium compounds, as well as enhanced beneficial effects of these other materials.

It has also been found that selenium compositions of the present invention demonstrate an anti-microbial action when administered as a dilute aqueous solution or in an inert cream or ointment.

Research by the applicant suggests a possible explanation for the effect of the selenium compound of the present invention on body tissue, particularly with respect to the ability to reduce the severity from and improving the recovery from physically-induced damage to body tissue. Tests have shown that as the selenium compounds are administered in accordance with the present invention, there is an increase in selenium throughout the host's body, including in blood tissue.

It has been found that red blood tissue, like the skin tissue observed in the examples herein, obtain greater resistance to trauma when the selenium content is increased in accordance with the present invention. In FIG. 1, the % hemolysis of red blood tissue in a human host is plotted as a function of sodium chloride concentration and selenium ingestion. Normally, as sodium chloride concentration decreases, the osmotic pressure on red blood tissue increases causing trauma to such tissue which is manifested as increased hemolysis. After ingestion of selenium, % hemolysis and therefore trauma is reduced. FIG. 1 shows the % hemolysis as measured at different sodium chloride concentrations for a human host under normal diet and for the same human host after about seven days of ingesting orally sodium selenite at a daily dosage of 0.5 mg of elemental selenium. The Table shows that after the ingestion of selenium, the % hemolysis of the blood tissue descreased demonstrating greater resistance to trauma. One possible explanation is that as selenium content of blood increases, there is a corresponding increase in the selenium-containing enzyme gluthatione peroxidase, which tends to afford greater protection to membrane phospholipids from normal oxidative damage. While this selenium enzyme has not been isolated in body tissue other than blood tissue, its presence has been suspected. The observation of reduced ecchymosis in both blood and other body tissue caused by trauma and the rapid recovery of both blood and other body tissue from trauma suggests that the apparent mechanism in blood tissue described above may also be present in other body tissue.

The primary active ingredient in the therapeutic compositions of the present invention is the selenium compounds. It is to be noted that selenium occurs in a number varying valence forms. For example, selenium compounds in which the selenium has a +4 valance or a +6 valence, usually as the selenite and selenate ions, may be utilized in the compositions of this invention. Among the selenite and selenate forms, the preferred compounds utilized in the compositions of this invention are the water soluble alkali metal salts thereof, and particularly, the sodium and potassium salts, that is, sodium and potassium selenite and selenate. On the other hand, organic compounds of selenium may also be utilized in the compositions of this invention. For example, selenium compounds of cystine and methionine, as well as the aliphatic mono- and di-selenodicarboxylic acids having about 7 to 11 carbons in the carbon chain may be used. Particularly useful acids of this group include monoseleno-11,11'-di'n-undecanoic acid, diseleno-4,4'-di-n-valeric acid and diseleno-11,11'-di-n-undecanamide. It is to be understood, however, that the particular organic forms of selenium compounds set forth herein are not to be considered limitative. Other organic selenium compounds which exhibit the desired activity and are compatible and non-toxic can be used in the practice of this invention.

It is a critical aspect of this invention that the selenium in the form present in the composition be capable of being absorbed by the tissue of the body to be treated. It is noted that water insoluble selenium compounds are not generally absorbed on this level.

The compositions of this invention can be made by mixing a suitably appropriate carrier and the selenium compound together and agitating the mixture until homogeneity is attained.

The concentration of the selenium compound to be present in a particular composition will depend upon the means of administration and nature of the composition. For example, compositions for topical administration should have generally a lower concentration of elemental selenium than compositions for other types of administration.

The selenium compound can be present in such an amount so that the elemental selenium concentration of the therapeutic composition is in the order of from about 0.005 to about 2 mg per gram of the total weight of the composition. The concentration, of course, depends upon the therapeutic activity desired and toxicity maximum levels.

As the daily dosage range is of the order of about 0.05 to 2.0 mg and preferably 0.5 to about 1.0 elementalselenium, it is convenient as a practical matter to formulate the composition so that about 0.5 mg to about 1.0 mg of elemental selenium is present in a given dosage amount of the composition.

The compositions of the present invention are quite stable and can be pre-mixed in the form of subsequent administration. Art recognized techniques for packaging, storing and preparing medicinal composition for administration are generally applicable to these compositions.

As noted above, the therapeutic compositions in accordance with the present invention may be made in various physical forms for well known methods of administration. For example, the composition can be in a suitable form for injectable, topical, suppository and oral administration. The choice of the particular carrier or vehicle and other additives present will depend upon the form desired. Said compositions may also be combined with other materials such as cleansing and antiseptic-type agents.

In carrying out the practice of this invention, a wide variety of carriers or vehicles for the selenium can be utilized and the terminology "pharmaceutically acceptable carrier or vehicle" as employed throughout this specification and in the appended claims is to be understood to include any known carriers or vehicles generally employed in the pharmaceutical field including inert and active carriers or vehicles. The vehicles or carriers should not detrimentally affect any of the active ingredients of the composition.

Exemplary inert carriers or vehicles include: sugars and milk sugars, such as lactose; liquids, such as water, isotonic aqueous solutions, saline solutions and alcohol; and inert powders, creams, salves, ointments, cleansing and antiseptic agents and the like.

Pharmaceutically active carriers or vehicles may also be used. These may include physiologically active powders, liquids, salves, creams and ointments as well as materials such as vitamins, steroids including cortisone and hydrocortisone. Other materials include proteolytic enzymes, such as those obtained from the pineapple plant and sold under the trade name of Ananase by William H. Rorer, Inc. of Fort Washington, Pa., USA, proteolytic enzymes obtained from the papaya plant and sold under the trade name of Papase by Warner/Chilcott, Division of Warner-Lambert Company of Morris Plains, N.J., USA, and others, such as animal pancreas extracts which contain trypsin and chymotrypsin, one form of such extract being sold under the trade name of Chymoral by Armour Pharmaceutical Co. of Phoenix, Ariz., USA.

For oral administration, the therapeutic composition of the present invention can be prepared in dosage forms as capsules, tablets, powders, syrups, oral solutions and the like. These orally administrable compositions may contain such additives as diluents, fillers, lubricants and glidants. Where they are in the form of a liquid, they should be suitably prepared so that the ingredients including the liquid pharmaceutical carrier are bland to the gastric mucosa.

In the case of the injectable form of the composition, the therapeutic selenium compound may be dissolved in distilled or sterilized water to form a parenteral preparation, or it can be mixed with intravenous infusions such as glucose or saline.

In accordance with this invention, selenium can be utilized in compositions suitable for topical, dermatological applications. In this regard, the selenium compounds can be used for skin treatments and maintenance in dermatological creams, salves, and the like. Such compositions can be effective in treating skin irritations, certain rashes, dermatitis, eczema, acne, and pruritus, and providing anti-microbial action. Such compositions also have properties making them useful in reducing the rate of cell aging due to exposure to light and oxygen which generally results in an oxidizing condition that weakens the cell membranes, thus causing the cells to deform. In this regard, it is to be noted that the number of damaged cells generally increases rapidly with the time of exposure to light and oxygen. However, the use of dermatological preparations containing selenium in accordance with this invention dramatically interrupts or stops such damaging effects.

The topical forms of the compositions of the present invention are also particularly effective in improving and accelerating the healing of tissue damaged by burns, which includes burns caused by the sun, heat, electricity, radioactive exposure and chemicals.

It is also to be noted that selenium compositions in accordance with the invention prevent distortion or adverse bio-chemical effects in cells which are subjected to ultraviolet light which greatly damages the membrane of such cells.

The composition of the present invention may be administered as eye drops in the form of a very dilute isotonic aqueous solution, that is, from about 0.1 mg to 0.5 mg of elemental selenium per cc solution and properly buffered to substantially neutral pH of about 6–7. Such eye drop solutions are useful in relieving eye irritation and redness caused by dust, smoke, smog, wind and sun glare, swimming, strain due to reading and television viewing or in the problems encountered in adapting to the utilization of contact lenses. A daily dosage of such an eye drop solution would be in the order of 1/20 to 1/5 cc.

It is to be understood that the particular carriers or vehicles set out above are illustrative only and other known pharmaceutically acceptable materials can be utilized in the compositions of this invention so long as they do not react with the selenium and other active ingredients to destroy the identity thereof. Moreover, the particular carrier or vehicle chosen for use will depend upon the form of the composition needed for the particular method of administration and the host to receive the composition.

In those cases where the composition contains more than about 1.0 mg by weight, the composition may be employed in the form of divided dosages when being administered whether it be in the form of a tablet, a capsule or a liquid solution. Moreover, a particular dosage in this respect can be administered several times a day so long as the total amount of selenium compound does not exceed the generally accepted maximum of about 2.0 mg per day.

In some instances, the composition of this invention can be made by simply mixing the selenium compound in proper proportion with an appropriate carrier. For example, in preparing tablets, an alkali metal selenite or selenate salt in its dry form may be mechanically mixed with a powdered carrier or vehicle and shaped or pressed into tablets or encapsulated by known art recognized techniques. On the other hand, if desirable, such salts can be dissolved in water and then mixed with a powdered carrier and shaped or pressed into tablets.

As an alternative, liquid compositions can be prepared simply by dissolving the selenium compounds in water and using the composition in that form with recognized additives for either external or oral application. The materials as mixed should contain at least a 0.05 mg of selenium to achieve most therapeutic benefits and may contain up to an amount conveniently combinable with the carrier to provide a daily dosage of selenium in a range of from about 0.05 mg to about 2.0 mg, and preferably from about 0.5 mg to about 1.0 mg.

While the stated range is generally a beneficially useful amount of selenium in accordance with this invention, it is also to be understood that this range is normally the amount given to an adult mammalian individual. However, dependent upon the weight and age of an adult mammalian host, the amount ingested by such a host may be adjusted accordingly within the stated range or somewhat outside the minimum and maximum thereof. The total overall amount to be ingested per day by a relatively small or young individual, for example, is preferably near the lower end of the range and for larger or older individuals, toward or in the area of the upper end of the stated range. A general range for daily treatment dosages, again based upon the purpose of treatment and other factors of the individual, would be in the range 0.005–0.02 mg per kg weight of the host.

In using the selenium compositions of this invention with the view to obtaining the pre-operative and post-operative benefits thereof, the compositions may simply be administered orally to an adult patient or host in divided doses for several days, e.g., from 1–7 days, preceding surgery in the stated concentrations or for several days, e.g., from 1–7 days following the surgical procedure or other trauma. For example, an aqueous solution of sodium selenite or sodium selenite can be made in a concentration to provide 5.0 mg of selenium and then sub-divided by dilution to provide an equivalent amount of selenium of 0.5 to 1 mg and administered in daily amounts orally or otherwise for a period of 1–5 days preceding and following surgery. On the other hand, the selenium may also be administered orally, intraveneously or subcutaneously, for example, by dissolving sodium selenate or sodium selenite in water in an amount such that one drop of the solution yields 0.33 mg of selenium. The concentration may be based upon one drop of the solution being equal to 1/20 of a cc. More dilute and concentrated solutions may also be used.

In accordance with the present invention, the effectiveness of selenium is generally enhanced by administering the same simultaneously with other physiologically active materials. For example, compositions in accordance with this invention can comprise small amounts of selenium combined with Vitamin E, wherein the Vitamin E is present in the range from about 10 I.U. to about 1000 I.U., and preferably from about 200 I.U. to about 800 I.U. The combination permits advantageous beneficial effects due to the presence of selenium with the vitamin, it being understood that in use further appropriate dilution takes place so that the daily amount of elemental selenium administered does not exceed 1.0 mg.

The selenium can also be combined with ascorbic acid, i.e., Vitamin C and utilized in the pre-treatment of patients undergoing elective surgery. Due to the fact that some selenium does form a precipitate with the Vitamin C, an appropriate method of administration should be used to minimize this precipitation effect.

The present invention presents many advantages both in its therapeutic effects and in the ability to formulate administrable compositions. When ingested, selenium is distributed to all of the cells in the body and is stored nonselectively but not uniformly, as is the case with several other elements such as chromium, iodine, and calcium.

Compositions of this invention are relatively simple to prepare. The water soluble sodium and potassium salts of selenium are readily available and are easily incorporated into a suitable pharmaceutical carrier or vehicle without the need for extraordinary and elaborate manufacturing equipment. Moreover, if desirable, the selenium salts can be distributed in a suitable carrier and stored for long periods of time without loss of effectiveness. On the other hand, if desired, the salts can be marketed separately and simply mixed or compounded with a carrier just prior to use. Numerous other advantages of this invention will be readily apparent to those skilled in the art.

Numerous modifications of this invention may be made without departing from the spirit and scope thereof. Accordingly, it is to be understood that this invention is not to be limited to the illustrative embodiments set forth herein.

EXAMPLE 1

This example is presented to illustrate the tolerance and effect of compositions of the present invention as administered to humans. The patient chosen for this example was 22 years old. Some four years prior to receiving the treatment in accordance with the present invention, he had undergone a rhinoplasty surgery which resulted in severe and alarming post-operative ecchymosis, edema and blood red eyes. The rhinoplasty surgical procedure involved the fracture of the patient's nose and associated trauma associated with the surrounding tissues. This prior treatment and recovery of the patient acts as a control to the instant example.

Four years after the aforementioned rhinoplasty surgery and after some three and a half years following complete recovery, the patient received the treatment in accordance with the present invention which contained 0.65 mg of selenium. This oral dosage was prepared as follows:

One ounce of sodium selenite as obtained from City Chemical Corp., of New York, N.Y., was added to ordinary tap water to yield a concentration of 28.35 mg of sodium selenite ($Na_2SeO_3$) to 1 cc of water. This is equivalent to 13.0 mg of elemental selenium per cc of water.

The foregoing solution was ingested in an amount daily to yield a daily dosage of 0.65 mg per day. The daily dosage was continued for a period of seven days. On the evening of the seventh day of treatment, the patient was involved in an automobile accident in which he suffered head, nose and facial injuries. This included a fracture of his nose and associated trauma to the surrounding tissue. The patient received emergency hospital treatment including examination and treatment by a plastic surgeon. During the course of the patient's recovery, there was no observed ecchymosis or edema of the nose, eyes or face, although trauma had been sustained as a result of the accident.

EXAMPLE 2

This example illustrates the effect of orally ingesting the therapeutic composition of the present invention on the irritation of the eyes of a human patient. The patient was a wearer of contact lenses and for many years suffered regular inflammation and irritation due to the wearing of contact lenses. The patient received by oral ingestion the therapeutic composition prepared in accordance with Example 1 in an amount equivalent to a daily dosage of 0.5 mg of selenium. After a period of 5 days, the redness and inflammation that was normally present in his eyes subsided and discontinued. After his eyes reached an optimum improvement, he discontinued the ingestion of the therapeutic composition for a period of seven days. After those seven days, the patient's eyes became inflamed, red and irritated to the same extent as existed prior to the original treatment with the therapeutic composition as noted above. A subsequent resumption in the ingestion of the therapeutic composition again improved the patient's eyes as during the prior treatment period. No side effects from this treatment have been observed.

What is claimed is:

1. A therapeutic method for reducing or inhibiting edema in the skin tissue of humans and for accelerating the recovery thereof, said method comprising administering to said human a composition comprising (i) a water soluble organic or inorganic selenium compound capable of being absorbed by the tissue to be treated to said human said inorganic compound selected from salts wherein the selenium is present in the form of selenate or selenite anions and the cation is pharmaceutically acceptable and said organic compound selected from the group consisting of selenium cystine, selenium methionine and aliphatic mono- and di-selenodicarboxylic acids having about 7 to 11 carbons in the carbon chain, and (ii) a non-toxic pharmaceutically acceptable carrier or diluent therefor;

said composition being administered so as to provide the equivalent of 0.05 mg–1.0 mg of elemental selenium per day to the host in single or multiple dose form by means selected from oral, topical, parenteral and intravenous infusion.

2. The therapeutic method of claim 1 wherein said selenium compound is an inorganic salt.

3. The therapeutic method of claim 2 wherein said selenium compound is an alkali metal salt.

4. The therapeutic method of claim 1 wherein said composition is administered topically to the area to be treated.

5. The therapeutic method of claim 4 wherein the composition is in the form of an ointment, salve or cream.

6. The therapeutic method of claim 4 wherein said selenium compound is an alkali metal salt.

7. The therapeutic method of claim 4 wherein said selenium compound is a silver selenate or silver selenite.

8. The therapeutic method of claim 1 wherein said therapy is administered to provide pre-operative or post-operative therapy for surgical patients to reduce or inhibit edema in skin tissue and to accelerate the recovery thereof.

9. A method for providing therapy in the treatment of burns of skin tissue in humans, said method comprising topically administering to said human in the area of the body to be treated a composition comprising (i) a water soluble organic or inorganic selenium compound capable of being absorbed by the tissue of said human being treated, said inorganic compound being selected from salts wherein the selenium is present in the form of selenate or selenite anions and the cation is pharmaceutically acceptable and said organic compound being selected from the group consisting of selenium cystine, selenium methionine and aliphatic mono- and di-selenodicarboxylic acids having about 7 to 11 carbon in the carbon chain, and (ii) a non-toxic pharmaceutically acceptable carrier or diluent therefor;

said composition being administered so as to provide the equivalent of 0.05 mg–1.0 mg of elemental selenium per day to the host in single or multiple dose form.

10. The method of claim 9 wherein the composition is in the form of an ointment, salve or cream.

11. The method of claim 9 wherein said selenium compound is an inorganic salt.

12. The method of claim 9 wherein said selenium compound is an alkali metal salt.

13. The method of claim 9 wherein said selenium compound is a silver selenate or silver selenite.

14. A therapeutic method for alleviating irritation and redness in the eyes of humans, said method comprising administering to each eye from 1/20 cc to 1/5 cc of an eye drop solution comprising a water soluble organic or inorganic selenium compound capable of being absorbed by the tissue of the eye being treated, said inorganic compound selected from salts wherein the selenium is present in the form of selenate or selenite anions and the cation is pharmaceutically acceptable and said organic compound selected from the group consisting of selenium cystine, selenium methionine and aliphatic mono- and di-selenodicarboxylic acids having about 7 to 11 carbons in the carbon chain, and wherein said selenium compound is dissolved in a suitably buffered isotonic aqueous solution whereby the concentration of the compound in solution is in the range of about 0.1 mg to 0.5 mg of elemental selenium per cc of solution.

15. The therapeutic method of claim 14 wherein said eye drop solution is administered in an amount to provide a daily dosage from about 0.05 to 0.5 mg of elemental selenium.

16. The therapeutic method of claim 14 wherein said selenium compound is an inorganic salt.

17. The therapeutic method of claim 14 wherein said selenium compound is an alkali metal salt.

18. A therapeutic method for reducing or inhibiting ecchymosis in the skin tissue of humans and for accelerating the recovery thereof, said method comprising administering to the host a composition comprising (i) a water soluble organic selenium compound capable of being absorbed by the tissue to be treated of the host, wherein the selenium is present in the form of selenate or selenite anions and the cation is pharmaceutically acceptable and said organic compound selected from the group consisting of selenium cystine, selenium methionine and aliphatic mono- and di-selenodicarboxylic acids having about 7 to 11 carbons in the carbon chain, and (ii) a non-toxic pharmaceutically acceptable carrier or diluent therefor; said composition being administered so as to provide the equivalent of 0.05 mg–1.0 mg of elemental selenium per day to the host in single or multiple dose form by means selected from oral, topical, parenteral, and intravenous infusion.

19. A topical therapeutic composition for administration to human skin tissue for the purpose of reducing the severity from and accelerating the recovery from physically induced damage to skin tissue caused by means including burns, said composition being in the form of an ointment, salve or cream and comprising (i) a water soluble organic or inorganic selenium compound capable of being absorbed by the tissue of the host being treated, said inorganic compound selected from salts wherein the selenium is present in the form of selenate or selenite anions and the cation is pharmaceutically acceptable and said organic compound selected from the group consisting of selenium cystine, selenium methionine and aliphatic mono- and di-selenodicarboxylic acids having about 7 to 11 carbons in the carbon chain, and (ii) a non-toxic pharmaceutically acceptable carrier or diluent therefor;

wherein the elemental selenium concentration of the composition is about 0.005 to 2 mg. per gram of the total weight of the composition.

20. The topical composition of claim 19 wherein said selenium compound is an alkali metal salt.

21. The topical composition of claim 19 wherein said selenium compound is a silver selenate or silver selenite.

* * * * *